United States Patent [19]

Bianchi et al.

[11] Patent Number: 4,814,348
[45] Date of Patent: Mar. 21, 1989

[54] THERAPEUTIC COMPOSITIONS CONTAINING DERIVATIVES OF ACRYLIC ACID HAVING AN OXYGEN-CONTAINING HETEROCYCLE, THERAPEUTIC TREATMENT THEREWITH AND NEW COMPOUNDS

[75] Inventors: Mario Bianchi, Carate Brianza; Fernando Barzaghi, Monza, both of Italy

[73] Assignee: Roussel Uclaf, Paris, France

[21] Appl. No.: 52,972

[22] Filed: May 22, 1987

Related U.S. Application Data

[60] Division of Ser. No. 765,539, Aug. 14, 1985, Pat. No. 4,694,019, which is a continuation-in-part of Ser. No. 572,458, Jan. 20, 1984, abandoned.

[30] Foreign Application Priority Data

Jan. 24, 1983 [IT] Italy ............................. 19249 A/83
Aug. 25, 1983 [IT] Italy ............................. 22647 A/83

[51] Int. Cl.$^4$ ................................................ A61K 31/34
[52] U.S. Cl. ..................................... 514/469; 514/927
[58] Field of Search ................. 514/469; 549/436, 468

[56] References Cited

U.S. PATENT DOCUMENTS

| | | | |
|---|---|---|---|
| 2,532,579 | 12/1950 | Thomas | 167/27 |
| 2,562,208 | 7/1951 | Papa et al. | 167/30 |
| 3,753,997 | 8/1973 | Ash et al. | 260/296 R |
| 3,763,148 | 10/1973 | Ash et al. | 260/29 SR |
| 3,846,470 | 11/1974 | Raube et al. | 260/46 SE |
| 3,910,959 | 10/1975 | Vallet | 260/340.5 |
| 3,940,404 | 2/1976 | Ash et al. | 260/296 R |
| 3,940,487 | 2/1976 | La Croix et al. | 424/282 |
| 3,953,463 | 4/1976 | Ash et al. | 260/295 R |
| 4,017,517 | 4/1977 | Murata et al. | 260/340.5 |

FOREIGN PATENT DOCUMENTS

| | | |
|---|---|---|
| 1282644 | 9/1962 | Fed. Rep. of Germany . |
| 2047806 | 4/1972 | Fed. Rep. of Germany . |
| 2103749 | 8/1972 | Fed. Rep. of Germany . |
| 2501834 | 7/1975 | Fed. Rep. of Germany . |
| 1566213 | 5/1969 | France . |
| 2132354 | 11/1972 | France . |
| 1566212 | 7/1973 | France . |
| 2270856 | 12/1975 | France . |
| 55-36434 | 3/1980 | Japan . |
| 591415 | 9/1977 | Switzerland . |
| 0532822 | 1/1941 | United Kingdom ................ 549/468 |
| 588108 | 6/1947 | United Kingdom . |
| 1387733 | 3/1975 | United Kingdom . |
| 2061934 | 5/1981 | United Kingdom . |
| 2075836 | 11/1981 | United Kingdom . |
| 2107714 | 5/1983 | United Kingdom . |

OTHER PUBLICATIONS

Chimie Therapeutique 1975, No. 10, pp. 182 et seq. Aurozo et al.
Chemical Abstracts, vol. 95, No. 13, 28 Sep. 1981, p. 722, No. 115689k "Addition and acylation in the reactions of ethylzine compounds with unsaturated cyclic dicarboxylic acid anhydrides."
Chemical Abstracts, vol. 87, No. 13, 26 Sep. 1977, p. 571, No. 101785m "Direction of the nucleophilic attack on the ethylene bond of beta-aroyl-and beta-hetaroylacrylic acids."
Journal of American Pharmaceutical Association, vol. 37, No. 11, Nov. 1948, pp. 439-449.
Chemical Abstracts, vol. 88, No. 5, Jan. 30, 1978 Abstract 37442p.
Journal of the American Chemical Society, vol. 71, No. 4, Apr. 1949, F. K. Kirchner et al., pp. 1210-1213.
Journal of the American Chemical Society, vol. 70, No. 10, Oct. 1948, D. Papa et al., pp. 3356-3360.
European Journal of Medical Chemistry Chimica Therapeutica, vol. 12, Jan.-Feb. 1977, pp. 17-20.
European Journal of Medical Chemistry Chimica Therapeutica, vol. 13, No. 3, May-Jun. 1978, H. Orzalesi et al., pp. 259-264.
Bellstein, vol. 19, p. 312.
Journal of Pharmaceutical Sciences, vol. 66, No. 4, Apr. 1977, pp. 466-476, Child, Ralph G., et al., "Fenbufen, a New Anti-Inflammatory Analgesic: Synthesis and Structure-Activity Relationships of Analogs".
Journal of Medicinal Chemistry, vol. 15, No. 9, Sep. 1972, pp. 918-922, Markovac, A., et al.,—"Antimalarials, 3, 2,6-Bis(aryl)-4-pyridinemethanols with Trifluoromethyl Substituents".
Journal of Organic Chemistry, vol. 35, No. 5, May 1970, pp. 1367-1376, Pettit, George R., et al., "Bufadienolides, 1., Introduction and Base-Catalyzed Condensation of Methyl Ketonds with Glyoxylic Acid".
J.A.C.S., vol. 46, No. 10, Oct. 1924, pp. 2319-2326 Rice, Grace Potter, "The Isomeric Esters of Para-Ethoxy-Benzoylacrylic Acid".
Chimie Therapeutique 1975, Aurozo et al., No. 10, pp. 182 et seq.
Cahiers de Synthese Organique, vol. 3, p. 102 Mathieu and Allais.
Chem. Abstracts, vol. 88, 1978, 88., 37442P.

Primary Examiner—Frederick E. Waddell
Attorney, Agent, or Firm—Stevens, Davis, Miller & Mosher

[57] ABSTRACT

The present invention relates to therapeutic compositions for the treatment of gastric disorders, said compositions containing a compound of the formula

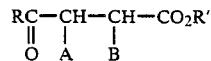

in which R is a mono- or poly-cyclic heterocyclic radical, possibly substituted, containing an oxygen atom, R' is a hydrogen atom or a linear, branched or cyclic alkyl radical, saturated or unsaturated, containing up to 18 carbon atoms, and,
either A represents a hydrogen atom and B represents a hydroxyl radical
or A and B together form a carbon-carbon double bond, as well as the pharmaceutically acceptable alkaline, alkaline-earth or amine salts thereof.

1 Claim, No Drawings

THERAPEUTIC COMPOSITIONS CONTAINING DERIVATIVES OF ACRYLIC ACID HAVING AN OXYGEN-CONTAINING HETEROCYCLE, THERAPEUTIC TREATMENT THEREWITH AND NEW COMPOUNDS

This is a division of application Ser. No. 765,539, filed Aug. 14, 1985, now U.S. Pat. No. 4,694,019, which in turn is a continuation-in-part of application Ser. No. 572,458, filed Jan. 20, 1984, now abandoned.

The present invention relates to therapeutic compositions containing derivatives of acrylic acid having an oxygen-containing heterocycle, therapeutic treatment therewith and new compounds.

The invention has as its object therapeutic compositions containing a gastric antisecretory and cytoprotective effective amount of a compound of formula I:

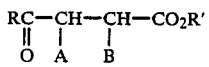

in which R is a mono- or poly-cyclic heterocyclic radical, substituted or unsubstituted, containing an oxygen atom, R' is a hydrogen atom or a linear, branched or cyclic alkyl radical, saturated or unsaturated, containing up to 18 carbon atoms, and,
  either A represents a hydrogen atom and B represents a hydroxyl radical
  or A and B together form a carbon-carbon double bond, as well as the pharmaceutically acceptable alkaline, alkaline-earth or amine salts of compounds of formula I in which R' represents a hydrogen atom and a pharmaceutically acceptable carrier.

By heterocyclic radical, there is to be understood, with the above proviso, preferably a furyl, pyranyl, benzofuranyl, isobenzofuranyl, chromanyl, isochromanyl, chromenyl, xanthenyl, phenoxathienyl, oxazolyl, isoxazolyl, furazanyl, phenoxazinyl, thieno (2,3-b)-furanyl 2H-furo (3,2-b)-pyranyl, benzoxazolyl or morpholinyl radical.

When the heterocyclic radical is substituted, it preferably bears as substituents one or more substituents selected from the group consisting of esterified or etherified free hydroxyl radicals in which the ester or ether portion contains from 1 to 18 carbon atoms, such as, for instance, the acetoxy radical or the methoxy radical, the ketone and oxime functions, linear, branched or cyclic saturated or unsaturated alkyl radicals having up to 18 carbon atoms, for instance, the methyl, ethyl, propyl or isopropyl radical, the ethenyl radical —CH=CH$_2$ or the ethynyl radical —C≡CH, the halogen atoms, such as fluorine, chlorine and bromine, and the CF$_3$, SCF$_3$, OCF$_3$, NO$_2$, NH$_2$ or C≡N groups.

When R' represents an alkyl radical, it is preferably a radical containing from 1 to 5 carbon atoms, for instance, the methyl, ethyl, n-propyl, isopropyl, n-butyl, isobutyl, terbutyl or n-pentyl radical.

The alkaline or alkaline-earth metal salts of the products of formula I, in which R' represents a hydrogen atom, may be the salts of sodium, potassium, lithium or calcium.

The amine salts of the products of formula I, in which R' represents a hydrogen atom, are the customary amine salts. Among the customary amines, mention may be made of monoalkylamines, such as, for instance, methylamine, ethylamine, propylamine, the dialkylamines, such as, for instance, dimethylamine, diethylamine and di-n-propylamine, and the trialkylamines, such as triethylamine. Mention may also be made of piperidine, morpholine, piperazine and pyrrolidine.

The compounds of formula I may exist in various possible stereoisomeric forms: the different stereoisomeric forms possible represent, in the case of the products of formula I in which A and B together represent a double bond, the E and Z (cis and trans) geometric isomers and, in the case of products of formula I in which A represents a hydrogen atom and B represents a hydroxyl radical, the racemic and optically active forms of these products.

4-(benzofuran-2-yl)-4-oxo-buten-2-oic acid is a known product. It has been described by Aurozo et al, in *Chimie Therapeutique* 1975, No. 10, page 182 et seq. However, no pharmacological property of this product has been described up to the present time. In their article, Aurozo et al describe the pharmacological properties of certain products, in particular the anti-inflammatory and hypercholesterolemizing properties. 4-(benzofuran-2-yl)-4-oxo-buten-2-oic acid is one of the products which are not shown to have interesting pharmacological properties.

As mentioned above, the compositions of the invention containing compounds of formula I in the different possible stereoisomeric forms, as well as the alkaline, alkaline-earth metal or amine salts of said products of formula I in which R' represents a hydrogen atom, have interesting pharmacological properties. In particular, they exhibit extensive anti-ulcer activity. Furthermore, placed in contact with the gastric mucosa, they exhibit gastric antisecretory and cytoprotective activity.

Among the preferred compositions of the invention are those containing compounds of formula I in which R' represents a hydrogen atom, as well as their pharmaceutically acceptable alkaline, alkaline-earth or amine salts, compounds of formula I in which A and B together form a carbon-carbon double bond, as well as the pharmaceutically acceptable alkaline, alkaline-earth or amine salts of these compounds when R' represents a hydrogen atom, and compounds of formula I in which R represents a furyl, pyrannyl, benzofuranyl, oxazolyl or isoxazolyl radical, possibly substituted, as well as the pharmaceutically acceptable alkaline, alkaline-earth or amine salts o, these compounds when R' represents a hydrogen atom.

The invention has still more particularly as its object the compositions containing the following compounds of formula I:
4-(2-oxo-4-hydroxy-6-methyl-2H-puran-3-yl)-4-oxo-buten-2-oic acid,
trans-4-(2,5-dimethyl-oxazol-4-yl)-4-oxo-buten-2-oic acid,
trans-4-(3,5-dimethyl-isoxazol-4-yl)-4-oxo-buten-2-oic acid,
trans 4-(5-methyl-2-furyl)-4-oxo-2-butenoic acid,
trans 4-(2,5-dimethyl-3-furyl)-4-oxo-2-butenoic acid,
trans 4-(3-furyl)-4-oxo-2-butenoic acid
as well as their pharmaceutically acceptable alkaline, alkaline-earth or amine salts.

The invention, in particular, also has as its object the compositions containing 4-(2-furyl)-4-oxo-buten-2-oic acid, as well as its pharmaceutically acceptable alkaline, alkaline-earth or amine salts.

The compositions of the invention are very useful in human therapy, in particular for the treatment of hyperchlorhydria, gastric and gastroduodenal ulcers, gastritis, hiatal hernia and gastric and gastroduodenal ailments accompanied by gastric hyperacidity.

The dose, which varies in accordance with the compound used and the ailment in question, may range, for instance, between 0.5 g and 2 g per day for adults, by mouth.

The above compositions are developed in such a manner as they can be administered by the digestive or parenteral route.

They may be solid or liquid and be present in the pharmaceutical forms currently used in human medicine, such as, for instance, simple or coated tablets, capsules, granules, suppositories and injectable preparations; they are prepared by the customary methods.

The active compound or compounds may be incorporated in excipients customarily employed in these pharmaceutical compositions, such as talc, gum arabic, lactose, starch, magnesium stearate, cocoa butter, aqueous or non-aqueous vehicles, fats of animal or vegetable origin, paraffin derivatives, glycols, various wetting, dispersing or emulsifying agents, and preservatives.

The invention also has as its object a method for the treatment of a patient suffering from hyperchlorhydria, gastric and gastroduodenal ulcers, gastrities, hiatus hernia or gastric and gastroduodenal ailments accompanied by gastric hyperacidity, comprising administering to said patient a gastric antisecretory and cytoprotective effect amount of a compound of the formula I.

The invention also has as its object new compounds of formula I:

in which R is a mono- or poly-cyclic heterocyclic radical, possibly substituted, containing an oxygen atom, R' is a hydrogen atom or a linear, branched or cyclic alkyl radical, saturated or unsaturated, containing up to 18 carbon atoms, and, either A represents a hydrogen atom and B represents a hydroxyl radical or A and B together form a carbon-carbon double bond, provided that if A and B together form a carbon-carbon double bond and if R' represents a hydrogen atom, R does not represent a benzofuran-2-yl group, as well as the pharmaceutically acceptable alkaline, alkaline-earth or amine salts of compounds of formula I in which R' represents a hydrogen atom.

The products of formula I can be prepared by a process in which there is subjected to the action of glyoxylic acid or of one of its alkyl esters of formula II:

in which R' is defined as above, a compound of formula III:

in which R retains its previous meaning, in order to obtain a product of formula $I_A$ corresponding to a product of formula I, in which A represents a hydrogen atom and B represents a hydroxy radical, or a product of formula $I_B$ corresponding to a product of formula I, in which A and B together represent a double bond and, possibly, the product of formula $I_A$ is subjected to a dehydrating agent in order to obtain the corresponding product of formula $I_B$, and, if desired, the product of formula $I_A$ which has been obtained is resolved into its optically active isomers and, if desired, the products of formula I obtained are salified or esterified in accordance with the customary methods.

By condensation of a product of formula II and a product of formula III, one obtains, depending on the operating conditions, particularly the pH, temperature and time of heating, a product of formula $I_A$ or a product of formula $I_B$, or a mixture of these products.

According to the different possible combinations of pH, temperature and time of heating, which are well known to the man skilled in the chemistry of aldolization, one obtains larger or smaller proportions of product $I_A$ or product $I_B$.

The products of formula $I_A$ are always formed first and the products of formula $I_B$ derived therefrom by dehydration.

In general, the proportion of product of formula $I_B$, which is formed directly, will increase when the operating conditions are such that the medium is more strongly acid (see, for instance, in Mathieu and Allais, *Cahiers de Synthese Organique*, Vol. 3, page 102, the passage concerning the chemistry of aldolization).

Under preferred conditions for the carrying out of the invention, the process described above is carried out as follows:

When it is desired to directly obtain a product of formula $I_B$, the reaction between the product of formula II and the product of formula III is carried out in a strongly acid medium. The acid medium may be obtained, for instance, by an excess of glyoxylic acid or by the presence of an acid, such as acetic acid, hydrochloric acid, sulfuric acid or phosphoric acid, or by the addition of sodium or potassium bisulfate.

For the direct preparation of product $I_B$, one can also operate, for instance, in the presence of acetic acid at about 130° C., in accordance with a process similar to that described in Japanese patent application No. 77 39 020 published on Oct. 3, 1977 (C.A. 88, 37442 p) or in *J. Med. Chem.*, 1972, Vol. 15, No. 9, 918–22. Glyoxylic acid may even be used, possibly, in the form of an alkali metal salt, such as the sodium or potassium salt.

When it is desired to obtain products of formula $I_B$, the condensation of the product of formula II with the product of formula III is preferably carried out at a temperature between 120° and 150° C. and heating is preferably effected for more than three hours.

It is well known that the "aldols" are very easily dehydrated into the corresponding unsaturated derivatives, either by heating or by treatment in acid medium, and that this dehydration can be effected either in a few minutes at high temperature, as described, for instance, in U.S. Pat. No. 3,953,463 (one to two minutes at 155° C.) or at lower temperature for a longer period of time.

When it is desired to obtain compounds of formula $I_A$, the condensation of the product of formula II with the product of formula III is preferably carried out at a pH greater than 6. This condensation is preferably effected at a temperature below 100° C., and preferably by heating for less than three hours.

When the compound of formula II in which R' represents a hydrogen atom is used, one may also advantageously operate at room temperature in the presence of a catalyst, such as an alkaline agent (sodium hydroxide, acid sodium carbonate or potassium hydroxide, for instance).

The condensation of the compound of formula II with the compound of formula III can be effected without solvent or in the presence of a solvent, such as an aromatic or aliphatic hydrocarbon (for instance, benzene, toluene or heptane).

The possible dehydration of a compound of formula $I_A$ into a compound of formula $I_B$ can be effected, for instance, by heating in acid medium.

Suitable dehydrating agents can, for instance, be one of the aforementioned acids.

The resolution of the racemic products of formula I into optically active isomers is effected by customary methods.

The alkaline, alkaline-earth or amine salts of compounds of formula I can be prepared by a customary process, such as, for instance, the action of corresponding bases on the said products of formula I or by double-decomposition or by any customary processes known for this type of $\alpha$-$\beta$-ethylene carboxylic acids.

The salification reaction is preferably carried out in a solvent or a mixture of solvents, such as water, ethyl ether, acetone, tetrahydrofuran or dioxan.

The compounds of formula I, in which R' represents an alkyl radical, can be prepared by a variant of the above process, in which an alcohol of the formula R'OH is reacted with the corresponding acid of formula I, preferably in acid medium. The acid may, for instance, be hydrochloric acid, phosphoric acid or para-toluene sulfonic acid.

The compounds of formula I, in which A and B together form a double bond, can be prepared by a variant of the previous process by reacting maleic anhydride with a compound of formula RH, in which R has the same meaning as previously indicated, in order to obtain the corresponding compound of formula I in which R' represents a hydrogen atom, which is subjected, if desired, either to the action of a base in order to form the salt thereof or to the action of an esterification agent in order to obtain a compound of formula I, in which R' represents an alkyl radical.

In one preferred embodiment:
the reaction of the compound of formula RH with maleic anhydride takes place in the presence of a catalytic amount of aluminum chloride;
the esterification is effected by means of an acid functional derivative, for instance, the acid anhydride or chloride, or else by reacting the acid and the alcohol in the presence of dicyclohexylcarbodiimide.

The following examples serve to illustrate the invention without, however, limiting it:

EXAMPLE 1

4-(benzofuran-2-yl)-4-oxo-buten-2-oic acid 6.4 g (0.04 mole) of 2-acetyl benzofuran and 3.68 g (0.04 mole) of glyoxylic acid monohydrate in 40 cc of glacial acetic acid are heated for 28 hours at the boiling point. The mixture is allowed to cool, and the product which deposits is removed by suction filtration and recrystallized from ethanol at 95° C. 3.2 g (37.4%) of the expected product are obtained. MP=182°–184° C.

This product is identical to Product 12 described by Alain Aurozo et al, *Eur. J. Med. Chem. Chimie Therapeutique*, Vol. 10 (1975), page 182 et seq.

EXAMPLE 2

4-(2-oxo-4-hydroxy-6-methyl-2H-pyran-3-yl)-4-oxo-buten-2-oic acid

A suspension of 2.52 g (0.02 mole) of 4-hydroxy-6-methyl-pyran-2-one and 6.6 g (0.05 mole) of anhydrous $AlCl_3$ in 20 cc of dichloroethane is treated with 1.96 g (0.02 mole) of maleic anhydride. The resultant solution is heated for 6 hours at the boiling point. The reaction mixture is cooled, poured over a mixture of ice and 2N hydrochodoric acid, and extracted with ethyl acetate. The organic phase is removed and dried over anhydrous sodium sulfate, filtered and brought to dryness. The residue is recrystallized from ethyl acetate. 1.2 g (26.8%) of the expected product is obtained. MP=228° C.

| Analysis: | | |
|---|---|---|
| Calculated: | C % 53.58 | H % 3.60 |
| Found: | 53.8 | 3.6 |

EXAMPLE 3

4-(2-furyl)-4-oxo-buten-2-oic acid

A mixture of 4.4 g (0.04 mole) of 2-acetyl furan, 3.68 g (0.04 mole) of glyoxylic acid monohydrate and 6.72 g (0.08 mole) of sodium bicarbonate in 60 cc of water is kept under agitation for 5 days at room temperature. The solution is passed over sulfonic resin to eliminate the salts and is evaporated to dryness. The oily residue is triturated in acetone. 0.8 g of a white solid is obtained by suction filtration (F=115°–135° C.). By evaporating the filtrate to dryness, one obtains 5.3 g (72%) of a clear oil which, in accordance with its NMR spectrum, is compatible with the product

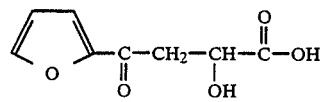

5 g of this oil (0.027 mole) is dissolved in a mixture of 100 cc of glacial acetitic acid and 10 cc of concentrated hydrochloric acid and heated at 60°–70° C. for 10 hours. The reaction mixture is cooled and brought to dryness and the residue chromatographed over silica by eluting with ethyl ether. By evaporation of the eluate, there are obtained 2.2 g (49%) of the expected product, MP=147°–150° C., which is recrystallized from dilute isopropanol. MP=158°–160° C.

| Analysis: | | |
|---|---|---|
| Calculated: | C % 57.84 | H % 3.64 |
| Found: | 57.7 | 3.6 |

EXAMPLE 4

Trans 4-(2,5-dimethyl-oxazol-4-yl)-4-oxo-buten-2-oic acid 11 g (0.079 mole) of 4-acetyl-2,5-dimethyl oxazol (described in *Chem. Ber.*, 84 96 (1951)) and 9.06 g (0.098 mole) of glyoxylic acid monohydrate are mixed with 110 cc of glacial acetic acid and kept at the boiling point for 10 hours. The mixture is then cooled, concentrated to dryness, taken up in 200 cc of water, acidified by the addition of 2N hydrochloric acid and left overnight. 4 g of the expected product are obtained upon suction filtration (MP=180°-182° C.) and recrystallized from ethyl acetate with treatment with activated charcoal. 2 g of the expected product are obtained. MP=183°-185° C.

| Analysis: $C_9H_9NO_4$ | | | |
|---|---|---|---|
| Calculated: | C % 55.38 | H % 4.65 | N % 7.18 |
| Found: | 55.62 | 4.58 | 7.11 |

EXAMPLE 5

Trans-4(3,5-dimethyl-isoxazol-4-yl)-4-oxo-buten-2-oic acid 3.8 g (0.027 mole) of 4-acetyl-3,5-dimethyl-isoxazole (described in *J. Am. Chem. Soc.*, 97 6489 (1975)) and 4.9 g (0.053 mole) of glyoxyllic acid monohydrate are mixed with 60 cc of glacial acetic acid and 6 cc of concentrated hydrochloric acid. The mixture is kept at the boiling point for 15 hours. It is then cooled and diluted with ice water and the crystals formed are filtered off, washed with water and dried. 2.2 g of the expected product are obtained, which are recrystallized from a mixture of benzene and ethyl acetate (3:1). MP=138°-140° C.

| Analysis: $C_9H_9NO_4$ | | | |
|---|---|---|---|
| Calculated: | C % 55.38 | H % 4.65 | N % 7.18 |
| Found: | 55.33 | 4.63 | 6.99 |

EXAMPLE 6

Trans 4-(5-methyl-2-furyl)-4-oxo-2-butenoic Acid 10 g of 2-acetyl 5-methyl furan (*J. Am. Chem. Soc.*, 72 3695 (1950)), 7.4 g monohydrated glyoxylic acid and 5 cm³ water are heated to 120°-130° C. for 5 hours, while eliminating the water formed in the course of the reaction. After cooling, 60 cm³ ethyl acetate are added and extracted with a solution of sodium carbonate. The aqueous phase is acidified, extracted with ethyl acetate, dried, and concentrated to dryness. The residue is chromtographed on silica, then, the product is recrystallized in ethyl acetate. 2.2 g of the expected product are obtained. MP=159°-162° C.

| Analysis: $C_9H_8O_4$ (180.16) | | |
|---|---|---|
| Calculated: | C % 60.72 | H % 4.70 |
| Found: | 60.00 | 4.48 |

EXAMPLE 7

Trans 4-(2,5-dimethyl-3-furyl)-4-oxo-2-butenoic Acid

As in Example 1, one starts out with 9 g of 3-acetyl 2.5-dimethylfuran (*J. Am. Chem. Soc.*, 70 739 (1948)), 6 g glyoxylic acid and 6 cm³ water. Following chromatography on silica (eluent: petroleum ether-ethyl acetate (2–8), recrystallization in ethyl acetate, 1.8 g of the expected product is obtained. MP=144°-147° C.

| Analysis: $C_{10}H_{10}O_4$ (194.19) | | |
|---|---|---|
| Calculated: | C % 61.93 | H % 5.28 |
| Found: | 61.85 | 5.19 |

EXAMPLE 8

Trans 4-(3-furyl)-4-oxo-2-butenoic Acid 1.5 g of 3-acetylfuran (Nippon Kagaku Zasshi 77 759 (1956)) (C.A. 1958, 348) and 1.25 g monohydrated glyoxylic acid and 0.5 cm³ water are heated to 100° C. for 1 hour and 30 minutes, while eliminating the water formed. The mixture is poured into a solution of sodium bicarbonate and extracted with ethyl acetate the initial product which is not reacted. The aqueous phase is acidified with 10% hydrochloric acid, extracted with ethyl acetate, then dried and concentrated to dryness. The residue obtained is chromatographed on silica, then recrystallized in an ethyl acetate/petroleum ether mixture. 280 mg of crystallized product are obtained. MP=104°-106° C.

The latter is dissolved in 6 cm³ of acetic acid containing 0.3 cm³ concentrated hydrochloric acid and heated to 60°-70° C. for 1 hour and 30 minutes. The residue is evaporated to dryness under reduced pressure, chromatographed on silica, and washed out with an ethyl acetate/petroleum ether mixture (2–8).

70 mg of the product are obtained, which crystallizes in ethyl acetate. MP=188°-191° C.

| Analysis: $C_8H_6O_4$ (166.14) | | |
|---|---|---|
| Calculated: | C % 57.84 | H % 3.64 |
| Found: | 57.58 | 3.68 |

PHARMACEUTICAL FORMS

EXAMPLE 9

Tablets

Tablets were prepared in accordance with the following formula:

| | |
|---|---|
| Product of Example 3 | 100 mg |
| Excipient q.s. for a finished tablet to | 300 mg |
| Product of Example 6 | 100 mg |
| Excipient q.s. for a finished tablet | 300 mg |

(Details of the excipient: lactose, wheat starch, processed starch, rice starch, magnesium stearate, talc.)

EXAMPLE 10

Capsules

Capsules were prepared in accordance with the following formula:

| | |
|---|---|
| Product of Example 3 | 100 mg |
| Excipient q.s. for a finished capsule to | 300 mg |
| Product of Example 7 | 100 mg |
| Excepient q.s. for a finished capsule | 300 mg |

(Details of the excipient: talc, magnesium stearate, aerosil.)

PHARMACOLOGICAL STUDY

A. Toxicity

The median lethal dose ($LD_{50}$) was evaluated upon oral administration of the products to mice.

The results obtained were as follows:

| | | |
|---|---|---|
| Product of Example 1 | $LD_{50}$ | 350 mg/kg |
| Product of Example 2 | $LD_{50}$ | 350 mg/kg |
| Product of Example 3 | $LD_{50}$ | 750 mg/kg |
| Product of Example 4 | $LD_{50}$ | 350 mg/kg |
| Product of Example 5 | $LD_{50}$ | 350 mg/kg |
| Product of Example 6 | $LD_{50}$ | 350 mg/kg |
| Product of Example 7 | $LD_{50}$ | 350 mg/kg |

B. Determination of the gastric antisecretory activity

The technique used is described by H. Shay et al in *Gastro. Enterology*, 5 43 (1945).

Male rats are used of a weight of about 200 g, which had been deprived of food for 48 hours, but with 8% glucose solution ad libitum. The pylorus of the rats, which had been slightly anesthetized with ether, is ligated and then, upon the end of the operation, the product to be tested is administered in different doses or, in the case of the control animals, an 0.5% solution of carboxymethyl cellulose is administered intraduodenally, whereupon the abdominal incision is sutured.

Three hours later, the animals are sacrificed and their stomachs removed after ligation of the esophagus.

The gastric juice is removed and centrifuged. The volume is then noted and the total acidity is determined on 100 μl of gastric juice by titration to a pH of 7 by means of 1/100N caustic soda.

The percentages of variation of total acidity of the gastric secretions are calculated, as compared with the results obtained with the control animals.

The results are as follows for a dose of 10 mg/kg:

| | |
|---|---|
| Product of Example 1 | 53% |
| Product of Example 2 | 70% |
| Product of Example 3 | 94% |
| Product of Example 4 | 77% |
| Product of Example 5 | 87% |
| Product of Example 6 | 75% |
| Product of Example 7 | 45% |

We claim:

1. A method for the treatment of a patient suffering from hyperchlorohydria, gastric or gastroduodenal ulcers, gastritis, hiatal hernia or gastric and gastroduodenal ailments accompanied by gastric hyperacidity, comprising administering to said patient a gastric antisecretory and cytoprotective effective amount of 4-(benzofuran-2-yl)-4-oxobuten-2-oic acid or its pharmaceutically acceptable alkaline, alkaline-earth or amine salts.

* * * * *